United States Patent [19]

Masilamani et al.

[11] 4,310,702

[45] Jan. 12, 1982

[54] SELECTIVE MONOCHLORINATION OF KETONES AND AROMATIC ALCOHOLS

[75] Inventors: Divakaran Masilamani, Morristown; Milorad M. Rogic, Whippany, both of N.J.

[73] Assignee: Allied Corporation, Morristown, N.J.

[21] Appl. No.: 172,798

[22] Filed: Jul. 28, 1980

[51] Int. Cl.³ .................. C07C 45/63; C07C 37/62; C07C 148/00
[52] U.S. Cl. .................................. 568/348; 568/709; 568/779; 568/393; 568/315; 568/33; 568/48; 568/726; 568/729; 568/730; 568/637
[58] Field of Search .......... 568/709, 779, 348, 48, 568/726, 729, 730, 637, 33, 315, 393

[56] References Cited

U.S. PATENT DOCUMENTS

| | | | |
|---|---|---|---|
| 3,542,882 | 11/1970 | Ashall et al. | 568/779 |
| 3,920,757 | 11/1975 | Watson | 568/779 |
| 4,180,651 | 12/1979 | Mark | 568/721 |

FOREIGN PATENT DOCUMENTS

| | | | |
|---|---|---|---|
| 2726436 | 12/1977 | Fed. Rep. of Germany | 568/779 |
| 1047058 | 11/1966 | United Kingdom | 568/779 |

OTHER PUBLICATIONS

Castelfranchi et al., Chem. Abst., vol. 48, #10650c (1954).
Bilik et al., Zrn Org. Chem. vol. 2, pp. 348–351.
Chem. Zentr, 1942, II, pp. 763–764.
Yasnitskii et al., Chem. Abst., vol. 76, #139952 (1972).
Chem. Abst., vol. 86, #139594r (1977).
Bondy et al., Chem. Abst., vol 52, #6158g (1959).
Serebryanyi et al., Chem. Abst., vol. 66, #10737k (1967).

*Primary Examiner*—Natalie Trousof
*Assistant Examiner*—James H. Reamer
*Attorney, Agent, or Firm*—Alan M. Doernberg; Robert A. Harman; Gerhard H. Fuchs

[57] ABSTRACT

Sulfuryl chloride is reacted in the liquid phase with an organic reactant which is a ketone or aromatic alcohol unsubstituted on both ortho carbons in the presence of a moderator selected from the group consisting of aliphatic alcohols of 1–3 carbons and aliphatic ethers of 2–6 carbons, with sufficient moderator being present to selectively produce a product substantially free of compounds with more than one chlorine atom per carbonyl or aromatic hydroxy. The products, such as monochloroacetone, monochlorocyclohexanone, monochlorophenol and 2,2-bis(3-chloro-4-hydroxyphenyl)propane, are useful as chemical intermediates and as monomers for flame retardant polymers.

12 Claims, No Drawings

SELECTIVE MONOCHLORINATION OF KETONES AND AROMATIC ALCOHOLS

BACKGROUND OF THE INVENTION

The present invention relates to the selective chlorination of ketones and aromatic alcohols and particularly to chlorination with sulfuryl chloride wherein it is desired to maximize products having one chlorine added per carbonyl or aromatic hydroxy.

Chlorinations of organic compounds having functional groups such as ketones, aldehydes and aromatic hydroxies are known generally to produce mixtures of products with different depths of chlorination, i.e. mixtures of monochloro, dichloro and polychloro products.

Sulfuryl chloride is a well-known chlorinating agent for such reactions. While certain substituted molecules preferrentially give monochlorinations, unsubstituted ketones and aromatic hydroxies generally give a mixture of products. This is particularly true of compounds wherein both carbons adjacent the aromatic hydroxy or carbonyl are unsubstituted in the sense of having a hydrogen covalently bonded to each carbon in aromatic molecules and at least two hydrogens covalently bonded to each carbon in nonaromatic compounds such as ketones.

Examples of compounds which react with sulfuryl chloride to form monochlorinated products preferrentially are those wherein one of the two adjacent carbons is substituted: in the case of aromatics such that no hydrogen is present to chlorinate on an ortho carbon, and in the case of ketones such that one of the adjacent carbons is covalently bonded to two other carbons besides the carbonyl and only to one hydrogen, thus being a tertiary carbon whose hydrogen is preferrentially replaced by chlorine. An example of such substituted phenyls is ortho-cresol which is selectively monochlorinated by sulfuryl chloride. An example of a substituted ketone is methyl, i-propyl ketone which is selectively chlorinated to methyl, 1-methyl,1-chloro ethyl ketone.

Certain sulfur-containing compounds are known to affect the chlorination of certain organic compounds and especially phenyls, by sulfuryl chloride. Thus, in work by Bilik et al. in Zhurnal Org Khim. volume 5, number 2, pp. 348-51 (Feb. 19, 1969) and British Pat. No. 1,047,058 certain sulfhydryl compounds are said to moderate the reaction of phenyls with sulfuryl chloride so as to increase the selectivity to monochlorination. Other sulfur compounds are indicated as increasing the reaction rate and the selectivity towards parachlorination in U.S. Pat. No. 3,920,757, while such compounds are said to act as catalysts in Belgium Pat. No. 827,912 abstracted in chemical abstracts 85:123581C.

BRIEF DESCRIPTION OF THE INVENTION

It has been discovered that aliphatic alcohols and aliphatic ethers moderate the chlorination of ortho-unsubstituted ketones and aromatic alcohols by sulfuryl chloride so as to selectively monochlorinate such organic reactants. Accordingly, the present invention includes a chlorination method which comprises reacting in the liquid phase sulfuryl chloride with an organic reactant which is a ketone or aromatic alcohol unsubstituted on both ortho carbons in the presence of a moderator selected from the group consisting of aliphatic alcohols of 1-3 carbons and aliphatic ethers of 2-6 carbons, with sufficient moderator being present to selectively produce a product substantially free of compounds with more than one chlorine atom per carbonyl or aromatic hydroxy.

The ketones are of the formula

wherein R' and R" are each alkyl of 1-3 carbons or together are alkylene of 2-7 carbons optionally substituted by methyl. The aromatic alcohols are phenols of the formula

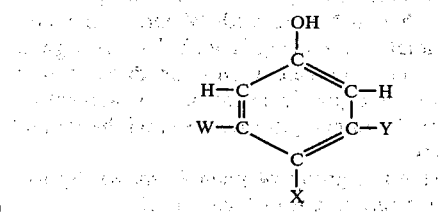

wherein W and Y are each H or alkyl of 1-3 carbons and X is H or is of the formula

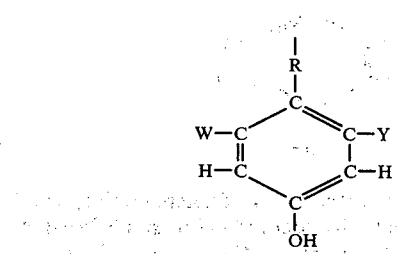

with R being a single bond, —O—, —S—, alkylene, —SO$_2$, —CO— or a cyclic moiety with both bonds to the same ring.

DETAILED DESCRIPTION OF THE INVENTION

The present invention relates to processes for chlorinating ketones and aromatic hydroxy-containing compounds such as phenols. In both cases, both carbons adjacent the hydroxy or carbonyl should be "unsubstituted" in the sense shown by formulas I and II as follows:

I

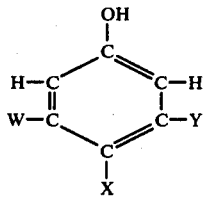

Of the ketones shown by formula I, preferred are the lower ketones where R' and R" are each alkyl of 1–3 carbons or together are alkylene of 2–7 carbons optionally substituted by methyl. Thus, representative preferred acyclic ketones include actone, methyl ethyl ketone, methyl propyl ketone, methyl n-butyl ketone, ethyl ethyl ketone and ethyl propyl ketone. Representative preferred cyclic ketones include cyclopentanone, cyclohexanone, cycloheptanone, cyclooctanone, cyclodecanone, 3-methyl cyclopentanone, 3-methylcyclohexanone and 4-methyl cyclohexanone.

Of the phenols shown by formula II, one preferred group is that wherein X is H, with W and Y (the meta positions) preferably also being H such that the organic reactant is phenol. Suitable mono- or di-substituted phenols (in the meta positions) include metacresol (3-methylphenol), 3,5-dimethylphenol, 3-ethylphenol and 3-propylphenol.

Another preferred group of phenols shown by formula II is one wherein X is of formula III

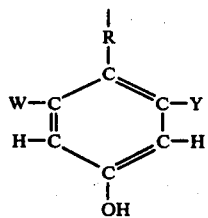

such that the organic reactant is a diphenol or bisphenol joined by an organic divalent radical or single bond R. R can be a single bond, —O—, —S—, alkylene, —SO₂—, —CO— or a cyclic moiety with both bonds to same ring carbon (as in phenolphthalein). Preferably R is alkylene of 1–4 carbons, either straight or branched, such as methylene, ethylidene, 2,2-propylidene or 2,2-butylidene, the latter being

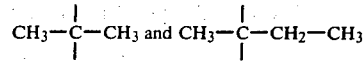

Preferably W and Y are H on both rings; and more preferably R is alkylene and W or Y are H such as in 2,2-bis(4-hydroxyphenyl)propane or bisphenol A.

The reaction is conducted by mixing the organic reactant, sulfuryl chloride and the moderator in a liquid phase at a suitable reaction temperature. For most of the present reactions, room temperature is a suitable reaction temperature. No catalysts, such as inorganic Lewis acids are required. Other suitable temperatures above or below room temperature can be determined by routine representation. The reaction mixture may contain only sulfuryl chloride, organic reactant and moderator (optionally in large excesses as the solvent) or may also contain an inert solvent such as dichloromethane or carbon tetrachloride or liquid sulfur dioxide. Preferred molar ratios of sulfuryl chloride to organic reactant are between about 1:10 and about 1.5:1 with about 1:2 to 1.1:1 being more preferred. For purposes of these ratios, when the reactant is a bisphenol, one mole of bisphenol should be considered two moles of reactant. The moderator may be present from small amounts (1% by moles of organic reactant) to large excesses as the solvent.

EXAMPLE 1

Dry sulfur dioxide (50 mL) was condensed into a flask containing 4.9 g (50 mmol) of cyclohexanone and methanol. The mixture was stirred at 0° to −2° and treated slowly with sulfuryl chloride over a period of 15–20 minutes. Gaseous HCl, sulfur dioxide and methyl chloride were given off. After stirring for a few minutes, the reaction mixture was quenched with 50 mL of chloroform. Sulfur dioxide was removed on a rotary evaporator and the chloroform solution was washed with saturated sodium bicarbonate solution and water. After drying over sodium sulfate, chloroform was removed and the crude product was analyzed by gas liquid chromatography (glc) (ov-1 10% on Chromsorb W-6-foot column). The product may be distilled if necessary. Table I shows the results obtained.

TABLE I

| | Cyclohexanone* as Reactant in Liquid Sulfur Dioxide | | | | | | | |
|---|---|---|---|---|---|---|---|---|
| Run | Sulfuryl Chloride (mmol) | Methanol (mmol) | Time (h) | Temp (°C.) | SM | 2CCH | 22DMC | 1M6CCH |
| A | 55 | 200 | 1 | −2 | 30% | 70% | T | T |
| B | 55 | 300 | 1 | 0 | 25% | 75% | T | T |
| C | 77 | 300 | 0.5 | 0 | 20% | ← | 80% | → |
| D | 62 | 300 | 16 | 0 | 20% | ← | 80% | → |
| E | 150 | 150 | 0.5 | 0 | 10% | ← | 90% | → |
| F | 62 | 225 | 0.17 | 0 | 0% | ← | 100% | → |
| G | 58 | 100 | 0.75 | −2 | 0% | 100% | — | — |

*50 mmol cyclohexanone 50 mL sulfur dioxide
T = trace,
SM = cyclohexanone starting material,
2CCH = 2-chlorocyclohexanone,
22DMC = 2,2-deimethoxycyclohexane,
1M6CCH = 1-methoxy,6-chlorocyclohexene

EXAMPLE 2

Sulfur dioxide (100 mL) was condensed into a flask containing 40 mL of dichloromethane (DCM), 9.8 g (100 mmol) of cyclohexanone and 9.6 g (310 mmol) of methanol. Sulfuryl chloride (14.6 g; 120 mmol) was added over a period of 30 minutes at 0° C. HCl, sulfur dioxide and methyl chloride were given off. After the addition of sulfuryl chloride was complete, the reaction mixture was poured into 500 mL of water containing 100 g of sodium hydroxide. The organic layer was separated and washed with water. After drying with sodium sulfate, dichloromethane was removed. 2-chlorocyclohexanone was isolated in 85–93% yield.

EXAMPLE 3

Cyclohexanone (4.9 g; 50 mmol) and sulfuryl chloride (6.75 g; 50 mmol) were dissolved in 50 mL of an organic solvent at −25° C. Alcohol was added in drops. Gas evolution was observed. The reaction mixture was then refluxed for an hour. After cooling, the reaction mixture was washed with saturated $NaHCO_3$ solution and water. After drying ($Na_2SO_4$), the solvent was removed. The products were identified by glc (OV-1 10% on Chromosorb W-6-foot column). The results are shown in Table II.

TABLE II

| Run | Solvent | Alcohol | SM | MCCH | DCCH | Other Products |
|---|---|---|---|---|---|---|
| A | DCM | Methanol 4.8 g | 100% | — | — | $ClSO_2OCH_3$, $CH_3Cl$, $SO_2$ |
| B | DCM | Methanol 1.6 g | 15% | 85% | — | HCl, $SO_2$, $CH_3Cl$ |
| C | DCM | IPA 3 g | 100% | — | — | IPC |
| D | CTC | IPA 3 g | 30% | 70% | — | HCl, $SO_2$, IPC |
| E | DCM | Methanol 1.6 g, water 1 g | T | 99% | T | HCl, $SO_2$, $CH_3Cl$ |

IPA = isopropyl alcohol,
IPC = isopropyl chloride
DCM = dichloromethane,
CTC = carbon tetrachloride
MCCH = monochlorocyclohexanone (principally 2-chlorocyclohexanone),
DCCH = dichlorocyclohexanone b.

EXAMPLE 4

Cyclohexanone and Ethers

Cyclohexanone (4.9 g; 50 mmol) was dissolved in an ether (50 mL) and maintained at 10°–15° C. Sulfuryl chloride (7.5 g; 56 mmol) was added in drops. The reaction was complete as soon as the $SO_2Cl_2$ was added. Samples were withdrawn and analyzed by glc (OV-1 10% on Chromosorb W-6-foot column). The work-up procedure was the same as described in Example 3. Results are shown in Table III.

TABLE III

| Run | Ether | SM | MCCH | DCCH |
|---|---|---|---|---|
| A | Ethyl ether | 0 | 85% | 15% |
| B | Tetrahydrofuran | 25% | 66% | 9% |
| C | p-Dioxane | 11.6% | 74.5% | 13.7% |
| D | Tetraglyme | 22% | 67.5% | 8.7% |

EXAMPLE 5

Phenol

Phenol (9.4 g; 100 mmol) and sulfuryl chloride (13.5 g; 100 mmol) were dissolved in 50 mL of dichloroethane. An organic base (ethers, alcohols, thioethers, sulfoxides, crown ethers) was added slowly. The reaction was exothermic and instantaneous. Gases were evolved (HCl, $SO_2$ and alkyl halides in the case of alcohols used as bases). The reaction mixture was refluxed for 1 hour. Samples were taken and analyzed by glc (OV-1 10% on chromosorb W-6-foot column). The reaction products were washed with saturated $NaHCO_3$ solution and water. After drying over sodium sulfate, the solvent was removed. Results are shown in Table IV.

TABLE IV

| Run | Moderator | SM | PCP | OCP | DCP |
|---|---|---|---|---|---|
| A | none | 100% | — | — | — |
| B | ethyl ether 7.4 g | 3% | 65.8% | 31.1% | — |
| C | methanol 3.2 g | 7.3% | 51% | 41.7% | T |
| D | ethanol 4.6 g | 10% | 60% | 30% | — |
| E | DMSO 48 g | 50% | 25% | 25% | — |
| F | dibutylsulfide 1.64 g | T | 66% | 33% | — |
| G | 10% 18-Crown-6 in 3 mL of DCM | 10% | 45% | 45% | — |

SM = phenol starting material,
PCP = parachlorophenol,
OCP = orthochlorophenol,
DCP = dichlorophenol (principally 2,4-dichlorophenol),
DMSO = dimethylsulfoxide

EXAMPLE 6

Bisphenol A

Bisphenol A (17.2 g; 75 mmol) dissolved in 100 mL of anhydrous ether was treated with sulfuryl chloride (22.25 g; 165 mmol) and stirred at room temperature. The reaction was exothermic, and the temperature initially rose to 30° C. However, HCl and $SO_2$ gases that were given off cooled the system and maintained it below 30° C. After the gas evolution had stopped, the reaction mixture was refluxed for 1 hour. The work-up procedure involved washing with saturated $NaHCO_3$ solution and water followed by drying ($Na_2SO_4$) and concentration. The product 2,2-bis(3-chloro,-4-hydroxyphenyl)propane was formed in 95% yield.

The reaction may be speeded up by adding 5.5 g of methanol to the ether solution of bisphenol A. Similar work-up showed 97% conversion. Recrystallization of the dichloro compound in pentane provides white crystals in 85% yield.

EXAMPLE 7

Acetone

Acetone (5.8 g; 100 mmol) and 9.6 g of methanol (300 mmol) were dissolved in 50 mL of $CH_2Cl_2$. $SO_2Cl_2$ (14.8 g; 110 mmol) was added in drops over 10 minutes. After the gaseous evolution (HCl, $SO_2$, $CH_3Cl$) had stopped, a sample was analyzed by glc (OV-1 10% on Chromosorb W-6-foot column). Only monochloroacetone and unreacted acetone peaks were observed. The reaction mixture may be refluxed (2 h), washed with saturated $NaHCO_3$, $H_2O$ and dried over $Na_2SO_4$. Concentration and distillation yields monochloroacetone in 85% yield. The rest of the product is mostly unreacted acetone and trace amounts of polychlorinated compounds and aldol condensation products.

In the absence of methanol, acetone reacts with sulfuryl chloride to form monochloroacetone and 2,2-dichloroacetone in the ratio of 2:1 in addition to unreacted acetone.

What is claimed is:

1. A chlorination method which comprises reacting in the liquid phase sulfuryl chloride with an organic reactant which is a ketone of formula I or a phenol of formula II,

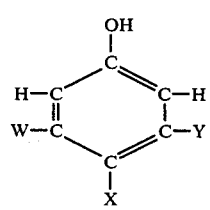   I

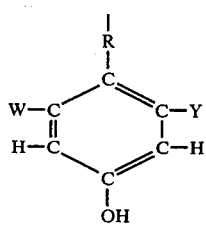   II wherein formula I, R' and R" are each alkyl of 1-3 carbons or together are alkylene of 2-7 carbons optionally substituted by methyl; wherein formula II, W and Y are each H or alkyl of 1-3 carbons, and X is H or of the formula

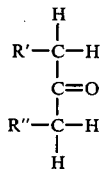   III with R being a single bond, —O—, —S—, alkylene, —SO$_2$—, —CO— or a cyclic moiety with both bonds to the same ring carbon in the presence of a moderator selected from the group consisting of aliphatic alcohols of 1-3 carbons and aliphatic ethers of 2-6 carbons, with sufficient moderator being present to selectively produce a product substantially free of compounds with more than one chlorine atom per carbonyl or aromatic hydroxy.

2. The chlorination method of claim 1 wherein the organic reactant is a ketone of formula I:

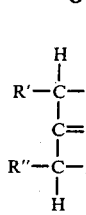   I with R' and R" being each independently H, alkyl of 1-3 carbons or together are alkylene of 2-7 carbons optionally substituted by methyl.

3. The chlorination method of claim 2 wherein the organic reactant is acetone.

4. The chlorination method of claim 2 wherein the organic reactant is cyclohexanone.

5. The chlorination method of claim 1 wherein the organic reactant is a phenol of the formula

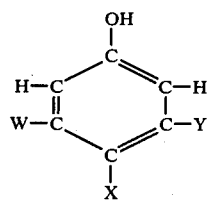   II wherein W and Y are each H or alkyl of 1-3 carbons, and X is H or is of formula III:

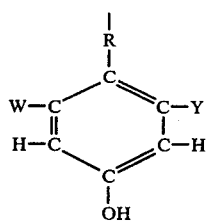   III with R being a single bond, —O—, —S—, alkylene, —SO$_2$—, —CO— or a cyclic moiety with both bonds to the same ring carbon.

6. The chlorination method of claim 5 wherein X is H.

7. The chlorination method of claim 6 wherein W and Y are H.

8. The chlorination method of claim 5 wherein X is of formula III and R is alkylene of 1-4 carbons.

9. The chlorination method of claim 8 wherein W and Y are H.

10. The chlorination method of claim 9 wherein the organic reactant is 2,2-bis(4-hydroxyphenyl)propane.

11. The chlorination method of claim 1 or 2 or 5 or 6 or 8 or 9 wherein the moderator is methanol.

12. The chlorination method of claim 1 or 5 or 6 or 8 or 9 wherein the moderator is an ether of 2-4 carbons.

* * * * *